US008696539B2

United States Patent
Popowski et al.

(10) Patent No.: US 8,696,539 B2
(45) Date of Patent: Apr. 15, 2014

(54) POSITIONING DEVICE AND A PROCEDURE FOR TREATING THE WALLS OF A RESECTION CAVITY

(75) Inventors: Youri Popowski, Geneva (CH); Erwin Berger, Stettfurt (CH)

(73) Assignee: Acrostak Corp. BVI, Winterthur (CH)

( * ) Notice: Subject to any disclaimer, the term of this patent is extended or adjusted under 35 U.S.C. 154(b) by 1242 days.

(21) Appl. No.: 11/794,944

(22) PCT Filed: Jan. 7, 2006

(86) PCT No.: PCT/EP2006/000077
§ 371 (c)(1),
(2), (4) Date: Jul. 10, 2007

(87) PCT Pub. No.: WO2006/074879
PCT Pub. Date: Jul. 20, 2006

(65) Prior Publication Data
US 2008/0045773 A1      Feb. 21, 2008

(30) Foreign Application Priority Data
Jan. 12, 2005   (EP) .................................... 05000516

(51) Int. Cl.
*A61N 5/00*   (2006.01)
(52) U.S. Cl.
USPC ........................................................... 600/3
(58) Field of Classification Search
USPC ....................................................... 600/1–8
See application file for complete search history.

(56) References Cited

U.S. PATENT DOCUMENTS

| | | | | |
|---|---|---|---|---|
| 4,963,128 | A | * | 10/1990 | Daniel et al. ........................ 600/7 |
| 5,316,016 | A | * | 5/1994 | Adams et al. ................... 600/587 |
| 5,913,813 | A | | 6/1999 | Williams et al. |
| 5,931,774 | A | | 8/1999 | Williams et al. |
| 5,993,374 | A | * | 11/1999 | Kick .................................. 600/8 |
| 6,022,308 | A | | 2/2000 | Williams |
| 6,083,148 | A | | 7/2000 | Williams |
| 6,413,204 | B1 | | 7/2002 | Winkler et al. |
| 6,673,006 | B2 | | 1/2004 | Winkler |
| 6,905,455 | B2 | * | 6/2005 | Rapach et al. ..................... 600/8 |
| 6,923,754 | B2 | * | 8/2005 | Lubock ............................. 600/3 |
| 7,776,310 | B2 | * | 8/2010 | Kaplan ........................ 424/1.25 |

(Continued)

FOREIGN PATENT DOCUMENTS
EP    1 402 922    2/2007

OTHER PUBLICATIONS
PCT/ISA/210 for PCT/EP2006/000077 dated Apr. 5, 2006.

*Primary Examiner* — Christine Matthews
(74) *Attorney, Agent, or Firm* — Buchanan Ingersoll & Rooney PC

(57) ABSTRACT

A positioning device (1) for treating the inner walls of a resection cavity, which was created by surgically removing of at least a portion of a tumor in a living body, characterized by the fact that the material of the device (1), part(s) of the device and accessories of the device (1) is (are) biologically degradable in the living body. Further a surgical procedure for treating a tumor in a living body of at least one of the former claims, comprising: (a) surgically removing at least a portion of said tumor thereby creating a cavity in the living body's remaining tissue; (b) placing a biodegradable treatment device in said cavity so that the degradable device occupies said cavity; and (c) treating tissue surrounding said cavity by means of said positioning device.

17 Claims, 7 Drawing Sheets

(56) References Cited

U.S. PATENT DOCUMENTS

| | | | |
|---|---|---|---|
| 2002/0022758 A1* | 2/2002 | Wolfson et al. | 600/6 |
| 2002/0103410 A1 | 8/2002 | Munro, III et al. | |
| 2002/0188166 A1* | 12/2002 | Viole et al. | 600/16 |
| 2003/0092957 A1 | 5/2003 | Scott et al. | |
| 2003/0159700 A1* | 8/2003 | Laufer et al. | 128/898 |
| 2005/0070753 A1* | 3/2005 | Forman et al. | 600/3 |
| 2005/0240073 A1* | 10/2005 | Apffelstaedt et al. | 600/2 |
| 2007/0191708 A1* | 8/2007 | Gerold et al. | 600/431 |

\* cited by examiner

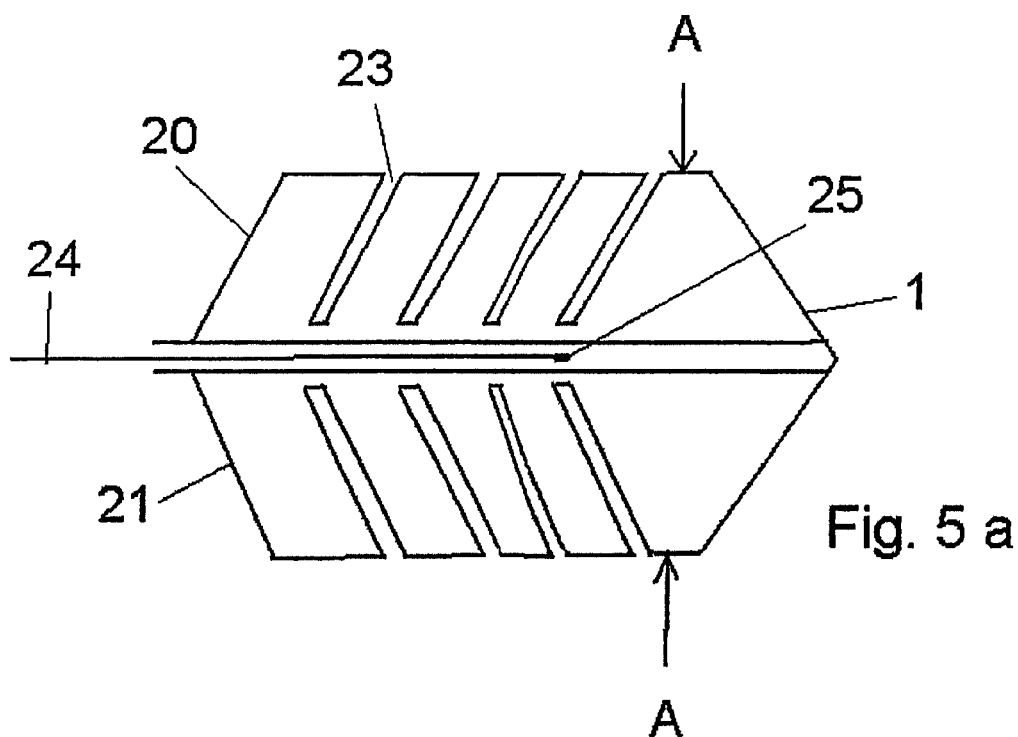
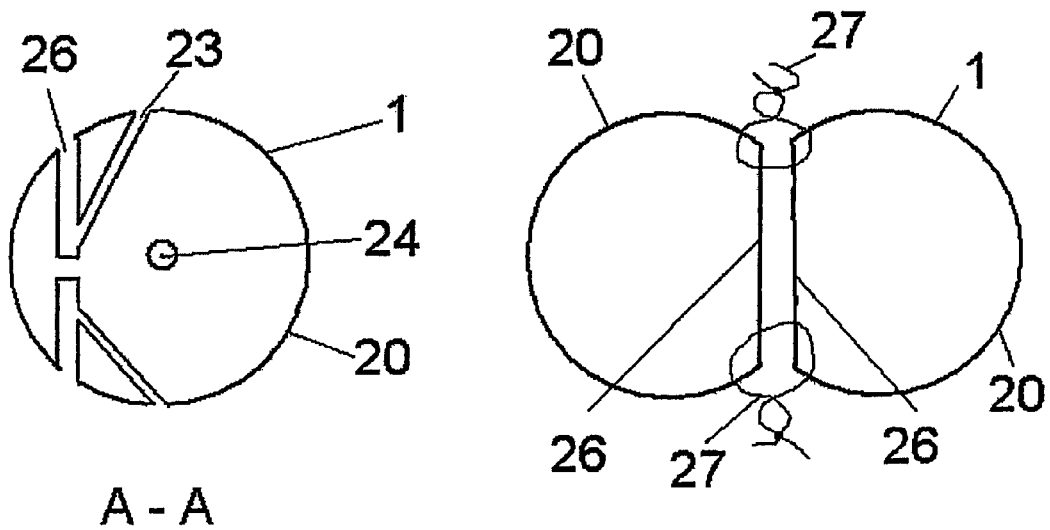
Fig. 5 a
A - A
Fig. 5 b
Fig. 5 c

POSITIONING DEVICE AND A PROCEDURE FOR TREATING THE WALLS OF A RESECTION CAVITY

DESCRIPTION

This invention relates to a positioning device and to a procedure for treating the walls of a resection cavity, which was created by the surgical removal of at least a portion of a tumor in a living body.

The treatment of tissues surrounding a cavity by the surgical removal of tumors has become increasingly sophisticated in the recent years, and improvements in surgical, chemotherapeutic and for instance brachytherapy techniques have led to better outcomes. A positioning apparatus for use with radiation therapy devices is delivered.

The concept of accelerated partial-breast irradiation is supported by recent pathologic data and the in-breast failure patterns reported after breast-conservation treatment. Several methods of partial-breast treatment have been established, including techniques utilising multiple catheters implantation, methods of single-fraction intra-operative radiation delivery and partial-breast external beam radiotherapy (Intensity Modulated Radiation Therapy). Multiple-catheter interstitial brachytherapy is presently probably the most widely used technique.

Historically the interstitial implantation of multiple catheters was heavily dependent on operator experience with possible variability in target coverage, homogeneity, and overall outcome. Improvements in the technique of catheter placement using various forms of image guidance coupled with 3D—dosimetry now provide the tools for reproducible catheter placement and improved outcome. Recently, advancement towards simplification of the brachytherapy procedures has been made with the clearance of a balloon catheter device. The balloon catheter is placed inside the lumpectomy cavity so that the surrounding breast tissue conforms to the balloon surface once the balloon is inflated. Treatment is prescribed and delivered to a circumferential volume, at 1 cm depth from the balloon surface, with either single central or multiple peripheral source(s) of high activity (high dose rate).

The early experience seems to show that this device provides reproducible, uniform target coverage with acceptable homogeneity and could be used in selected patients in order to avoid external radiotherapy following surgery. Convenience for the patient is maximized as these approaches deliver all of the radiation during a reduced period of time compared to external radiotherapy. This intraoperative approach has raised several questions. As the placement of the device is usually performed during or after the intervention, the availability of the final microscopic margin and axillary nodal status is not always available. Therefore, this information cannot be used to select patients for the appropriate treatment. Another possible disadvantage is that until recently only spherical balloon shapes were available, which do usually not conform to the various shapes of excised tissues (ovoid, tubular, etc.). Finally, when balloon catheter is implanted during the surgical resection, the catheter may be left in place during several weeks before the radiotherapy is performed. This may lead to surgical wound infection.

The document U.S. Pat. No. 6,673,006 discloses a spacing apparatus for use with radiation therapy devices and in particular, for use with brachytherapy device.

The document U.S. Pat. No. 5,931,774 describes implantable devices for treatment of proliferative disorders. The invention provides an implantable apparatus for treating a proliferative disorder in a patient. The device comprises a treatment fluid receptable for receiving a treatment fluid, an inflatable balloon having a balloon body, a catheter connected between the treatment fluid receptable and the balloon.

Further devices are known from the following documents: U.S. Pat. Nos. 6,413,204, 6,083,148, 6,022,308 and 5,913,813.

Some of these above mentioned known devices have a small diameter, adapted for intra-vascular treatments and are not usable for the present therapy. Some others have only one balloon of cylindrical shape type, delivering a non adapted dose to the complex shape of most targets. Finally, when expanded, a spherical balloon will be very close to the skin or to the thoracic wall, leading to possible short term (exsudation) or long term complications (telangectasia).

Therefore the purpose of this invention is to achieve a much more homogeneous dose delivery to resection cavity walls still completing treatment in a short period of time (5-10 days) with doses per fraction similar to those used with external partial breast radiotherapy or interstitial brachytherapy. The system could also be used to deliver a boost dose to the lumpectomy cavity before or after an external radiotherapy is performed, in young patients with breast cancer (<50 years), who being at higher risk for local recurrence necessitate higher local doses. The advantage, compared to existing balloon systems, lies in the fact that the surgeon may choose the best device shape which optimally suits to the resection cavity among various configurations. He may even cut or extend parts of the device. Once the device has been introduced inside the resection cavity, the margins of the lesion may be tightly sutured around the device. In some cases, the walls of the wounds could even be sutured on the device surface. Weeks or months later, according to the choosen therapeutic attitude (exclusive brachytherapy, or combined with external radiotherapy as a boost), the device will be used to deliver the treatment on the resection cavity margins that tightly surround the implant allowing optimal dosimetry.

In the case of breast cancer, the extent of breast tissue that should be treated after surgical resection of the primary lesion is probably better understood nowadays. When breast-conservation treatment was initiated in the 70ies, whole-breast irradiation was naturally applied as it duplicated the surgical target removed with mastectomy leading to loco-regional control rates comparable to those obtained by mastectomy alone. Long-term follow-up of multiple studies investigating this new breast-conserving treatment has proven the efficacy of post-lumpectomy whole-breast radiotherapy. It has been shown that surgery alone will result in >35% failure rates in some categories of patients at 10 years. However, it has been established as well that tangent fields used in whole breast radiotherapy may include excessive volumes of lung and heart leading to significant long term morbidity such as increased cardiovascular mortality. Some solutions were found such as heart sparing by treating left breast cancer during thorax inflation, but also by looking to additional selection criteria for breast radiotherapy. It has been shown that many locoregional recurrences result from the inadequacy of microscopic margin assessment, unrecognized multifocality of disease and/or unrecognized microscopic disease extent, etc. In addition, based on available relatively recent pathologic and clinical data, it seems that the target requiring treatment with adjuvant radiotherapy after lumpectomy for early stage breast carcinoma in some selected patients seems to be less than whole breast, and seems to be related, among others, to the extent of surgical resection as reflected by the measured microscopic margin.

For instance, the data suggest that a target for partial breast radiation defined as the lumpectomy cavity plus 1-2 cm margin after resection with negative microscopic margins could be appropriate in selected patients (>54 years, presenting with histologically negative nodes (pN0 sn, i+ allowed), histological tumour size <3 cm, excision margins >1 mm, apparently unifocal tumour, absence of histological multifocality, absence of extensive intraductal component (>25% DCIS in lesion), absence of peritumoral lymph or blood vessel invasion absence of lobular carcinoma, etc.).

In patients presenting with large T2-T3 prostate cancer, up to 50% of positive margins (cancer cells at the margin of resection) may be found after surgical resection. This may lead to elevated rates of locoregional recurrence with PSA values raising progressively in the following months or years. These patients will necessitate external radiotherapy to improve the local control rate immediately after surgical resection meaning they could have avoided surgical resection. Therefore, it could be advantageous to treat selectively the resection cavity left by the operator, avoiding the need for external irradiation. As prostate cancer cells are sensitive to elevated fractions of radiotherapy, a short treatment time with high fractions could be proposed (2-3 weeks) as for breast partial radiation.

The same situation is met with some brain tumors, such as glioblastomas, where negative margins are difficult to obtain because these tumors are very infiltrating. A brain implant may allow treating selectively the resection cavity walls, allowing in some situations to decrease or avoid external radiation.

The invention proposes a new positioning device and a procedure for treating the inner walls of a resection cavity, which was created by the surgical removal of at least a portion of a tumor in a living body. For example a new device for the treatment of the resection cavity, that will allow an optimal coverage of the inner surface of a cavity of the breast, prostate, brain, or any cavity in a living body created by the removal of a tumor.

The above mentioned problem was solved by the application of a biologically degradable material of the device, the parts of the device and/or the necessary accessories of the device of the invention.

Further was this problem solved by a surgical procedure for treating a tumor in a living body of at least one of the former claims, comprising: (a) surgically removing at least a portion of said tumor thereby creating a cavity in the body's remaining tissue; (b) placing a biodegradable positioning device in said cavity so that the degradable device occupies said cavity; and (c) treating remaining tissue surrounding said cavity by means of said treatment device. (d) prior to treatment, Xray, Ctscan, MR, Ultrasound or any appropriated imaging technique may be used in order to optimize treatment parameters.

Preferably the biologically degradable material is made from the following polymers:

Synthetic polymers such as poly(glycolic) acid, poly(lactic acid); in general: glycolic- and lactic acid based polymers and copolymers, poly caprolactones; in general: poly hydroxyl alkanoates (PHAs), (poly(hydroxy alcanoic acids)=all polyester), poly (ethylene glycol), poly vinyl alcohol, poly (orthoesters), poly (anhydrides), poly (carbonates), poly amides, poly imides, poly imines, poly (imino carbonates), poly (ethylene imines), polydioxanes, poly oxyethylene (poly ethylene oxide), poly (phosphazenes), poly sulphones, poly acrylic acids, poly methylmethacrylate (PMMA), poly acryl amides, poly acrylo nitriles, (poly cyano acrylates), poly HEMA, poly urethanes, poly olefins, poly styrene, poly terephthalates, poly fluorides, poly ethylenes, poly propylenes, poly ether ketones, poly vinylchlorides, silicones, poly silicates (bioactive glass), siloxanes (poly dimethyl siloxanes), hydroxyapatites, natural derived polymers such as poly aminoacids (natural and non natural), polyesters, poly β-aminoesters; in general: poly (peptides) such as albumines, alginates, cellulose, cellulosic biocomposites, cellulose acetates, chitin, chitosan, collagene, fibrine/fibrinogen, gelatine, lignine, starch composites with low, medium or high amount of starch; foamed starch, soy-based plastics, neutral polysaccharides (gellan gum, pullulan, laminarin and curdlan). Proteine based polymers such as poly (lysine), poly (glutamate), poly (malonates), poly (hyaluronic acids), poly nucleic acids, poly saccharides, poly (hydroxyalkanoates), poly isoprenoids, starch based polymers and that all copolymers thereof, as linear, branched, hyperbranched, dendrimers, crosslinked, functionalized (surface, functional groups, hydrophilic-hydrophobic).

Preferably the biologically degradable material is made from a biodegradable metal such as magnesium, or one of its alloys, that would degrade in several weeks or months. The structure may present as a scaffold or as a porous material.

Preferably the biologically degradable material is made from a combination of biodegradable metal such as magnesium or one of its alloys, together with the aforementioned polymers that would degrade in several weeks or months.

The biodegradable structure that occupies the resection cavity in a living body in order to deliver a therapy to the walls of the resection cavity.

A modular biodegradable structure that can be made from several subparts, that may be assembled or disassembled, cutted or grazed in order to be have the flexibility to vary the length, the width and the shape of the biodegradable structure to adapt as much as possible to the shape of the resection cavity and to be able to maintain an adequate position of the catheters through which the treatment will be performed.

A biodegradable structure that can modify its shape and/or volume inside a living body (decrease, increase diameter or length, modify its shape by a memory effect).

Preferably at least one radiopaque marker is arranged in the positioning device. For example one or two markers (is) are placed centrally in the positioning device, one on in the center or two on both ends of the positioning device. This will allow to see the place of the positioning device on Xray image, when the device cannot be seen as it can be seen on a MR or on a CT scan image.

The subclaims describe the possibilities of the application of the biologically degradable material.

Preferably the surgical procedure for treating a tumor in a living patient is applicable to a tumor being a brain, breast, prostate or any resected tumor cavity, wherein said device is further characterized as having a volume comparable to a volume of said cavity thereby avoiding any compression or distortion of normal surrounding tissue. If implant size is too important or not adapted, the surgeon may reduce the volume of the implant by cutting it to the adequate length or diameter before implanting the biodegradable material. Kits allowing to perform a size adaptation of the implant are available.

Furthermore the treatment is done non-invasively or with a minimally invasive approach without making further surgical incisions or with only tiny surgical incision on the living body. In the later case, the proximal end of the catheter may be left under the skin of the living body, allowing to extract the proximal end through a small incision several weeks or months after the tumor resection, and to catheterize this proximal catheter end to perform the therapy.

Furthermore a biodegradable device of any hollow shape (tube, cigar, etc.) may be inserted inside the resection cavity in order to allow a delayed introduction and positioning of a second therapeutic device days, weeks, months, after the intervention, inside a cavity well defined by the biodegradable structure. The second therapeutic device may be a catheter, a catheter with an expandable balloon, with a stent (self-expandable, balloon expandable, biodegradable) or any other structure that allows a well defined intracavitary therapy.

It is also possible to apply laser light to said remaining tissue surrounding said cavity by means of said treatment device or radiation to said remaining tissue surrounding said cavity by means of said treatment device or simultaneously laser light and radiation to said remaining tissue surrounding said cavity by means of said treatment device.

Another preferred procedure is that the physician evaluates the size of the lesion, makes a biodegradable mould of it, inserts adequately one to several catheters inside the molded biodegradable structure, and places the device inside the resection cavity. Such a system may be delivered as a kit.

Preferably the degradable device is made as a scaffold with a regular or irregular structure, or is made from a porous material or a foam with very small or very large pores or holes. A scaffold or foam made from polymer may be obtained for instance inside a mould through sub- or super-critical gas such as $CO_2$, or by a heat treatment at elevated temperatures, or by any other method known to someone skilled in the art. The holes of the scaffold, porous material or foam may also be isolated or continuous with each other. In the later case the structure allows diffusion of body fluids inside the device.

Where the device may have treatment catheter(s) which may either be displaced with regard to the device, or catheter(s) that may have a telescopic structure, allowing it (them) to be shortened or elongated easily after placing the implant. This should allow optimal positioning of one end of the catheter(s) close to the skin, when the implant is left totally inside the resection cavity of the living body (breast, perineal area, . . . ) for 4-8 weeks or longer (6-8 months), without any part of the device coming out. When the time of the therapy has come, an incision is made at the site where the catheter(s) arrive close to the skin to pull the catheter(s) out of the living body structure (breast, perineal area, . . . ) on the necessary distance, while enough catheter length remains at the level of the positioning device for an adequate therapy. These catheters may be used to introduce other brachytherapy catheters inside. Finally, after 5-10 days of therapy, the catheters that come out of the positioning system are removed by pulling them out, and the skin is closed. The adequate positioning of the implant in the cavity may be verified by imaging techniques such as MRI, ultrasound, CT-scanner, etc. This allows to adapt the dosimetry to the implant if it has expanded or shrinked several weeks or months after the intervention, and to treat patients taking into account the real geometric situation.

Where the device may have treatment catheter(s) which may have a loop, a screw eye on one end allowing to block the catheter with a suture when the said end is still inside the structure (breast, perineum, etc.).

Where the device may have treatment catheter(s) which may have an irregular surface on one end (such as a series of small knobs) allowing to block the catheter with a suture once the said end is pulled out from the structure (breast, perineum, etc.).

In another embodiment, the catheter and/or the positioning device may be impregnated and/or coated with anti-infective substances such as silver derivates (nanoparticules for instance), chlorhexidine derivates, heparine derivates, or any other substance decreasing the risk of implant and/or catheter infection known to someone skilled in the art.

In another embodiment, catheters may be positioned centrally in the biodegradable structure, or at its periphery, or placed on its outer surface. These catheters may run straight, along the positioning device axis. The catheters may also run around the positioning device in an helicoidal shape. This may be chosen according to radiation oncologist and surgeon preference, according to the resection cavity presentation and to dosimetric requirements.

Preferably the biodegradable positioning device may be inserted inside a resection cavity in order to allow better localization of the cavity to plan external radiotherapy. Indeed, after a resection, the residual cavity usually collapses and is filled with body fluids. By placing a biodegradable positioning device it will be easier to delineate the place where radiation has to be delivered by external therapy such as radiotherapy, microwave therapy, ultrasound. The tissues may be tightly sutured around the positioning device, in order to obtain a very well circumscribed volume.

Some examples of the invention are shown in the figures.

Figure 3:
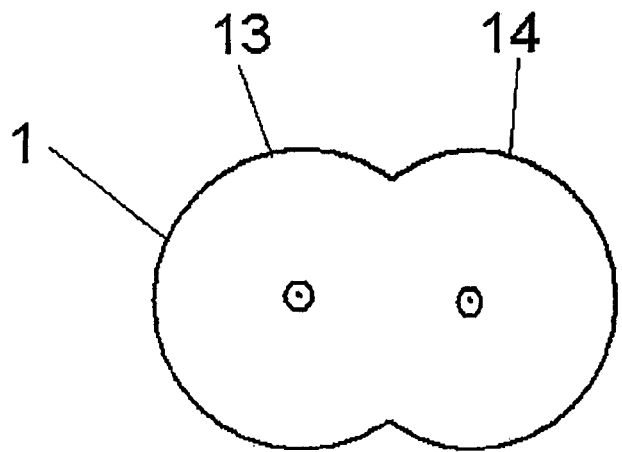
Figure 3:
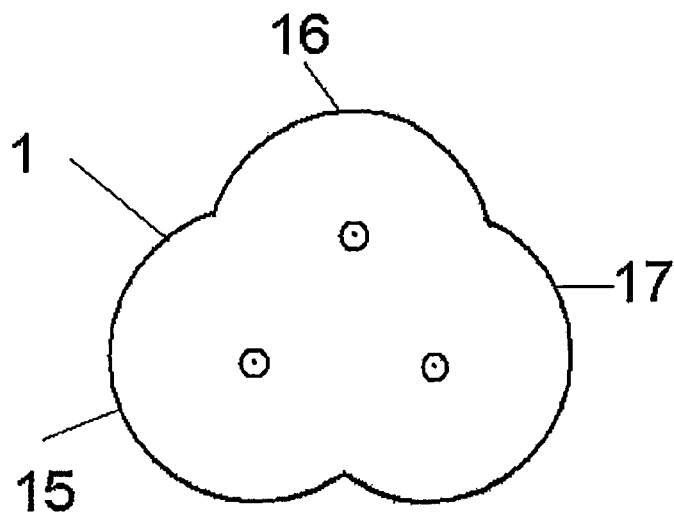
Figure 3:
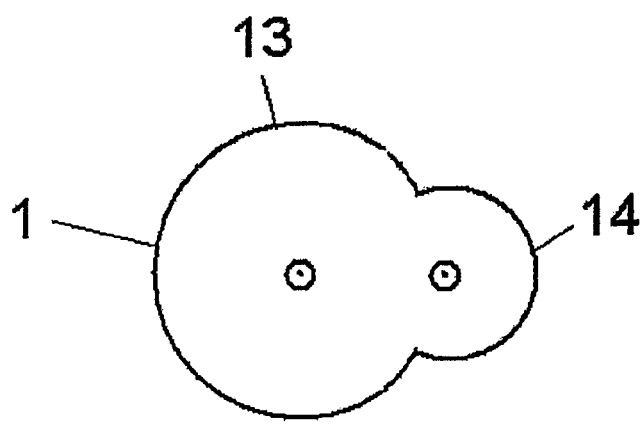

FIGS. 3 a-3 c show some combined shaped biodegradable devices.

Figure 4:
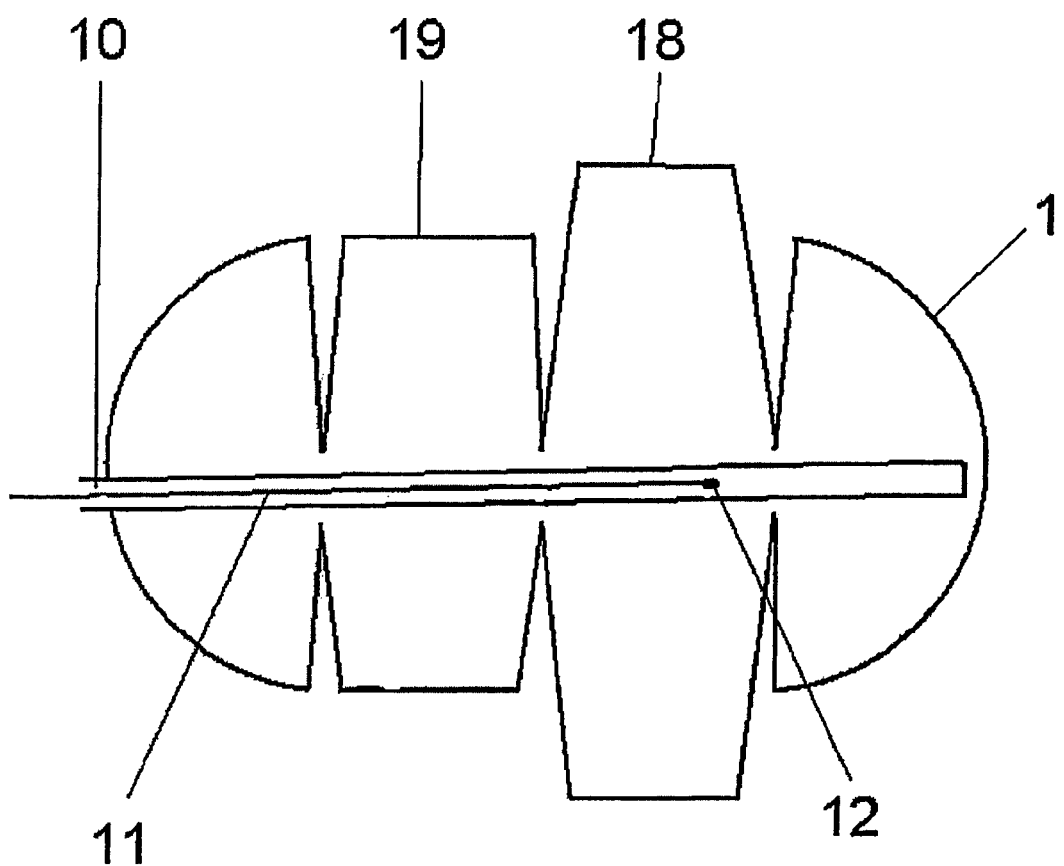

FIG. 4 shows another balloon device with sections of various diameters.

FIGS. 5 a-5 c show a specially designed device.

Figure 6:
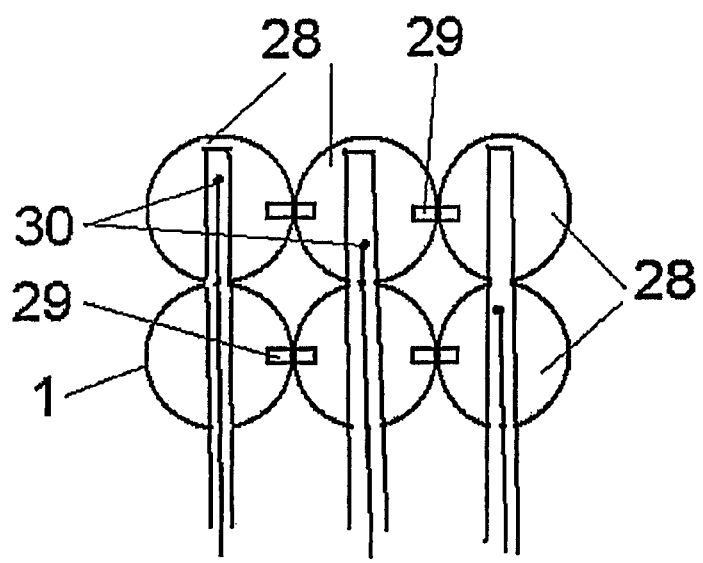

FIG. 6 shows a combination with beads.

Figure 7:
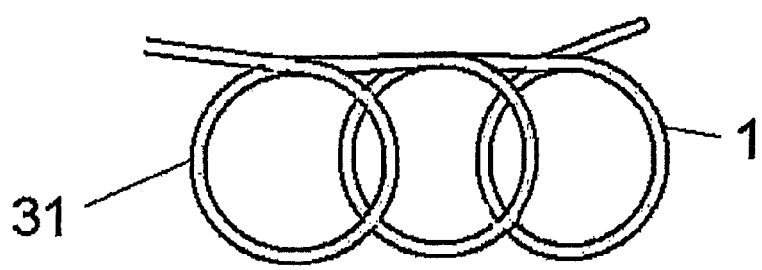

FIG. 7 shows a spiral formed device.

Figure 8:
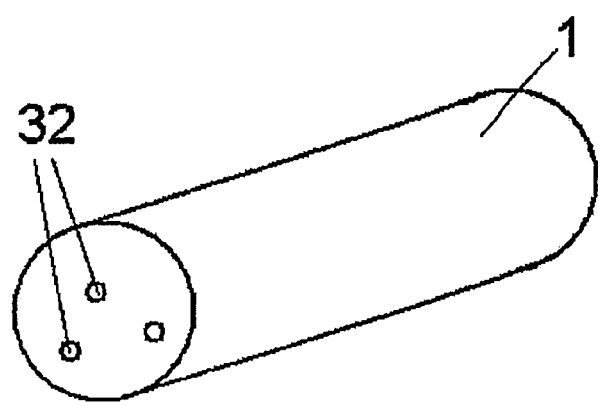

FIG. 8 shows an device with channels at the periphery

Figure 9:
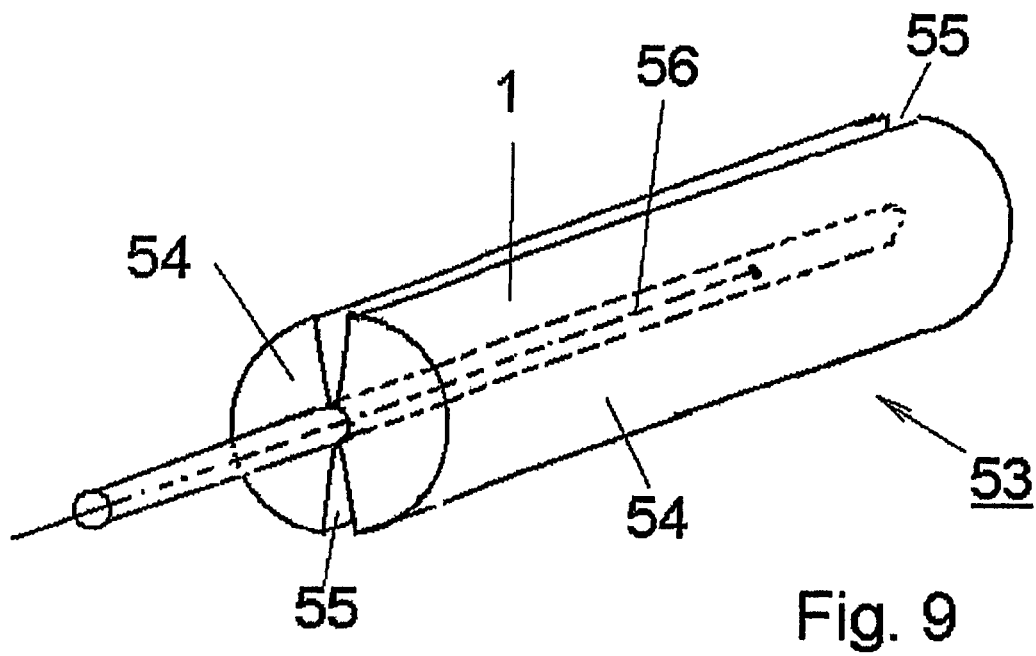

FIG. 9 shows a cylindrical biodegradable device with longitudinal waists

Figure 10:
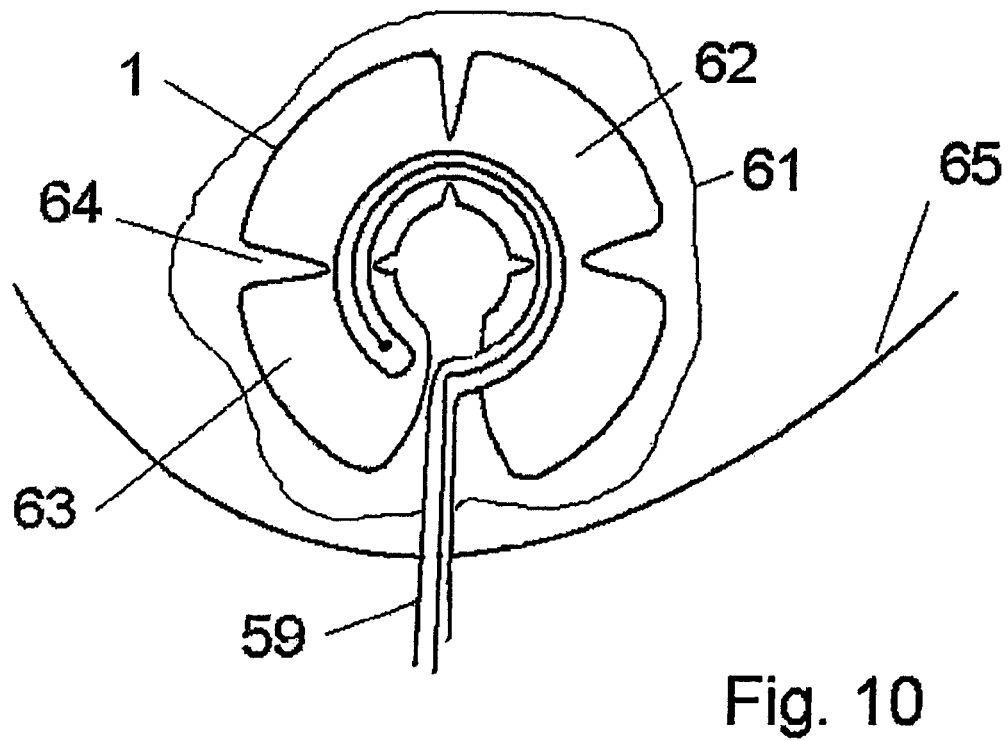

FIG. 10 shows a solution with a pre-molded shaft.

Figure 1:
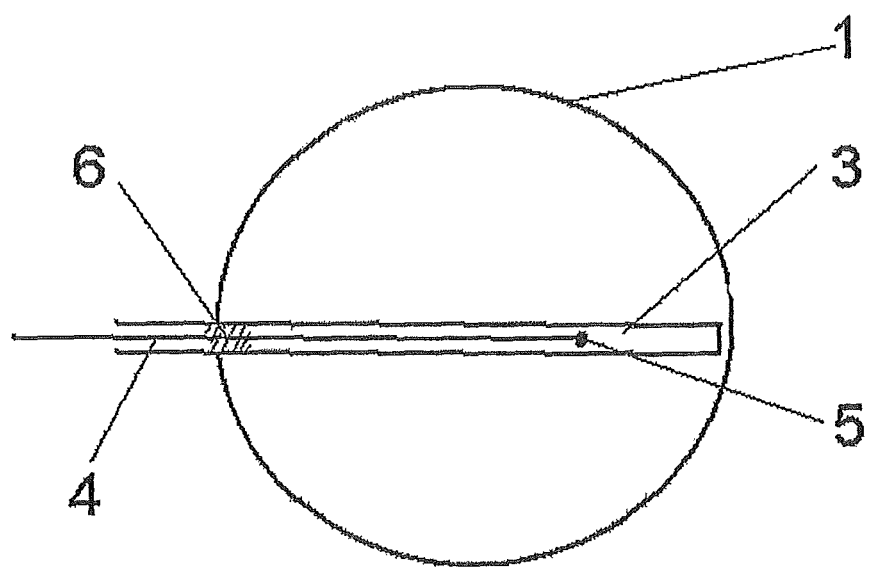
FIG. 1 represents a spherical biodegradable device.

FIG. 1 shows a device 1, for example a spherical biodegradable device. A lumen 3 is for a wire 4. At the top of the wire 4, a source 5 for radiation is situated. All kinds of radiation sources are possible, for example radioactive, infrared etc. The spherical device 1 is made of a biodegradable material. A part of the lumen 3 is unscrewed, for example by a thread 6, for leaving the biodegradable device 1 in the not shown cavity. The diameter of the spherical structure is in a range from 1 to 10 cm.

In one embodiment the biodegradable material is made from polylactic and glycolic acids. The proportion of glycolic acid varies between 0 and 100%, and preferably between 10 and 90%. 0% means a very slow degradation and 100% means a extremely rapid degradation of the material. Therefore the variation of the concentration of the glycolic acid make it possible to determine the degradation of the device and the stability of the shape of the device. For example the stability could vary between 30 days and more, a lot of variations are possible.

Figure 2:
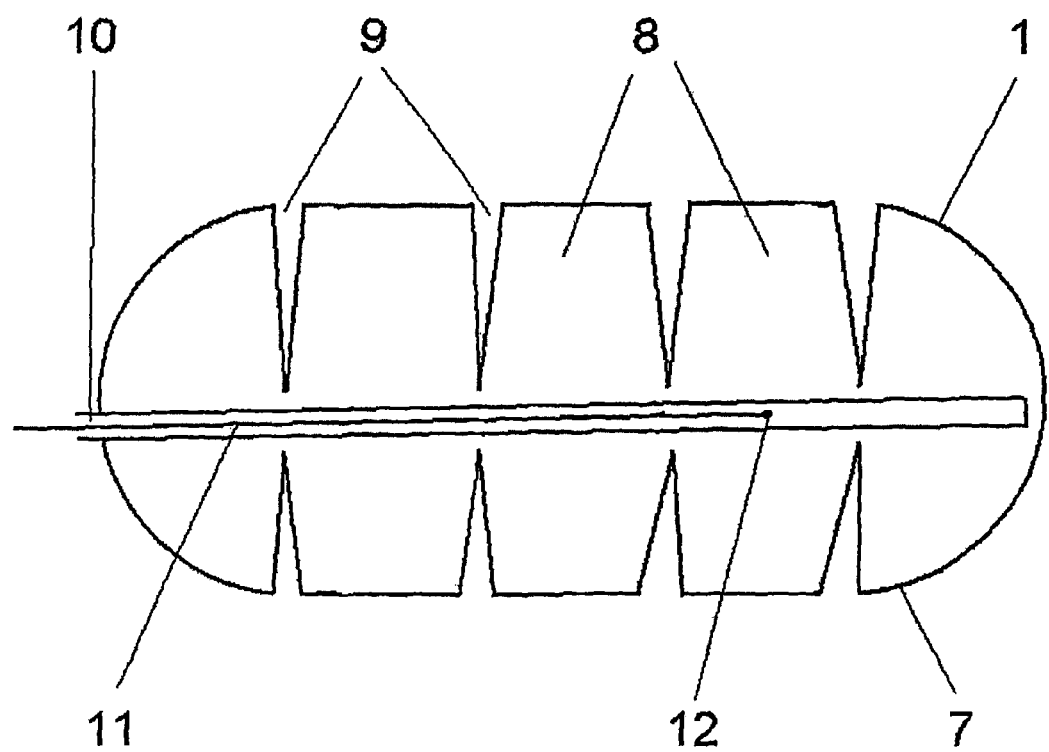
FIG. 2 shows a cylindrical shaped biodegradable device with sections.

FIG. 2 shows a cylindrical biodegradable device 1 with half-sphere shaped ends 7 device with at least one section. Here the device 1 consists of three sections 8, which are separated by waists 9. The lumen 10 for the wire 11 with the radiation source 12 is shown. When considering partial-breast irradiation, the data suggest that a target defined as the lumpectomy cavity plus 1-2 cm margin after resection with negative microscopic margins could be appropriate in selected patients (such as in patient with the material of the device is from biodegradable material. The length of the biodegradable structure is in a range from 1 cm till 10 cm. The diameter of the biodegradable structure or the section is in a range from 0.5 till 10 cm. The length of the biodegradable device may be modulated if needed by removing one or more of its sections.

The FIG. 3 a-FIG. 3 c shows three possible cross sections of possible biodegradable devices. FIG. 3 a is a combination of two devices 13 and 14 with the same diameter, FIG. 3 b is a combination of three devices 15, 16 and 17 with the same diameter. Self-evident the diameters of the devices 13 till 17 can be different, like in FIG. 3 c, where the diameter of the device 13 is larger than the diameter of the device 14.

The FIG. 4 shows a similar biodegradable device 1 like in FIG. 2. The diameter of the sections 8 can be different. In the figure the diameter of the section 18 is larger than the diameter of the adjacent sections 19. This allows to adapt to various resection cavity shapes such as cigar shape, conical shape, tubular shape, cylindrical shape, or any other shape known to anyone skilled in the art.

FIG. 5 a-FIG. 5 c shows a special biodegradable device 1. The device 20 in FIG. 5 a has triangle shaped ends 21. In the middle of the device 20 sections 22 are arranged. The ends 21 and the sections 22 are separated by inclined waists 23. The wire 24 has on its top a source 25. The section A-A of FIG. 5 a is shown in FIG. 5 b.

In FIG. 5 c two devices 20, cut at the position 26, are bound together with a filament 27.

The FIG. 6 shows a combination of six biodegradable beads 28, which are connected with biodegradable bridges 29. The advantage of this biodegradable device 1 is that it allows to adapt to any resection cavity shape. With this feature it is possible shape the device 1 and to adapt the dose of the radiation sources 30 to the cavity in an optimal way in order to reach better dosimetry.

FIG. 7 shows a spiral tube 31 as a biodegradable device 1. Another not shown device is a biodegradable coil which holds a catheter for holding the catheter apart from the tissue of the cavity.

FIG. 8 shows a cylindrical shaped biodegradable device 1 with at least 1 channel for a radiation source. Here are three channels 32 arranged in the periphery of the device. This allows to modulate the dose delivered to the resection cavity walls. A further possibility is a device like in FIG. 8, but where one or more catheter(s) are located near or on the outer surface of the positioning device. The catheters may run along the axis of the device or around the device, with angles still allowing catheterisation. A further possibility is to have a hole with a more important diameter (1 cm, 2 cm), allowing to insert a centering balloon catheter, several days, weeks, months, after the placement of the biodegradable cylinder has taken place.

Another biodegradable device 1 shows FIG. 9. In the FIG. 2 the waists 9 are radial directed. In FIG. 9 the biodegradable device 53 consists of two longitudinal sections 54 and waists 55, which are directed parallel to the axe 56. The FIG. 7 shows for example a cylindrical shaped device 53. Of course the feature of longitudinal directed waist is possible for several other shaped devices like in the former figures.

FIG. 10 shows a further biodegradable device 1 of the invention. Depending of the inner shape of the cavity 61, it is possible to pre-mold the positioning device in a desired shape. In FIG. 10 is shown a spherically shaped cavity 61 in a breast 65. The device 62 consists—as former mentioned devices—of device sections 63 with waists 64. In the middle of the device a shaft 59 is arranged. This shaft 59 is pre-molded. In this FIG. 9 the shaft has a circular shape. But all possible kinds of pre-molded shafts or device shapes (totally round for instance) are thinkable, depending of the inner shape of the treated cavity.

Furthermore a totally spherical shape without waists 64 of the device 62 in FIG. 10 is possible. This positioning device may be plain or hollow. All applicable shapes are feasible. For example a spherical shaped device with one or more catheter(s) running in its center or its periphery.

The above described features of the invention are merely exemplary and not limited. All thinkable shapes of biodegradable devices are possible. The main point is to find an appropriate shape for filling the cavity while allowing to obtain an optimal homogenous radiation treatment dosimetry.

The invention of this biodegradable device may be left in other places of the body, even for instance in the pelvic area, fixed on a pelvic wall, in order to allow an homogeneous dose distribution at an operated site, after the belly has been closed. It can be a structure as in FIG. 3a but with many structures in parallel, with 3, 4, or more catheters, covering a pelvic wall, or placed in a resection cavity like in the resection cavity of a resected prostate gland, or on a chest wall, after mastectomy has been performed.

Three further examples describe preferably the method of the invention:

EXAMPLE 1

A 60 years old patient presents with a ductal breast cancer lesion, 1 cm in diameter. A lumpectomy and an axillary dissection are performed which confirm the histology and the absence of axillary invasion. During the intervention, a cylindrical foam structure with a central catheter is introduced inside the resection cavity. The catheter is longer than the device. One of its ends is placed very close, just under the breast skin, but the whole structure remains completely inside the breast. Four weeks after surgery, a small incision is performed at the place where the catheter is very close to the breast skin. The catheter is pulled until 2.5 cm are coming out of the skin.

This external catheter is sutured to the margins of the lesion. A second catheter is inserted inside the central catheter and this second catheter is connected to an afterloader. A visible wire (for MR, US, X-ray, etc) is introduced inside the second catheter and orthogonal X-rays or a CT is performed in order to obtain an optimal dosimetry. Using an iridium source, a dose of 38.5 Gy total/10 fractions (3.85 Gy per fraction) is delivered. The treatment is prescribed at 1 cm from the device surface and is administered 2 times a day. After 5 days, the central catheter is removed and the skin is closed with one stitch. The patient is observed for recurrence and for complications.

EXAMPLE 2

A 45 years old patient presents with a ductal breast cancer comparable to the former one, but with 2 invaded lymph-nodes. She undergoes the same type of surgical resection and the placement of a biodegradable positioning device which will start degrading only after 6 months. After 6 sessions of chemotherapy, the patient undergoes 3 sessions of 5 Gy prescribed at 1 cm from the applicator surface. This corresponds to the boost, which needs to be delivered to the resection area as shown in the literature. After intracavitary radiation, the central catheter is removed and the patient starts the external radiation treatment, delivering 50 Gy to the whole breast with 2 tangential fields.

EXAMPLE 3

A 70 years old patient presents with a Gleason 6 prostate cancer, apparently limited to one lobe, and which can be felt by digital examination only in one lobe of the prostate. Surgical ablation is performed and possible positive margins are considered from the surgeon's opinion. A foam with 2 catheters is placed inside the resection cavity. After 5 weeks, the patient undergoes 12-14 sessions of very localized brachytherapy, on the side where capsular invasion was present. The PSA remains stable during follow up.

The invention claimed is:

1. A surgical procedure for treating a tumor in a living body, comprising:
    (a) surgically removing at least a portion of said tumor thereby creating a resection cavity in the living body's remaining tissue;
    (b) evaluating the size of the removed portion of the tumor;
    (c) making a biodegradable mold of the removed portion of the tumor to form a biodegradable positioning device having a pre-shaped molded body having a volume substantially equal to a volume of the resection cavity before insertion into the resection cavity;
    (d) placing the biodegradable positioning device, including the pre-shaped molded body having at least one tubular hole for allowing positioning of a therapeutic device, in said cavity so that the biodegradable positioning device occupies said cavity; and
    (e) inserting the therapeutic device in the at least one tubular hole; and
    (f) treating remaining tissue surrounding said cavity by the therapeutic device.

2. A surgical procedure for treating a tumor in a living body of claim 1, said tumor being a brain, breast, prostate or any resected tumor cavity, wherein said biodegradable positioning device has a volume no greater than a volume of said cavity thereby avoiding any compression or distortion of normal surrounding tissue.

3. A surgical procedure for treating a tumor in a living body of claim 1, wherein said treating is done non-invasively without making further surgical incisions on the living body.

4. A surgical procedure for treating a tumor in a living body of claim 1, wherein said treating is done minimally-invasively by making only small surgical incision(s) on the living body.

5. A surgical procedure for treating a tumor in a living body of claim 1, wherein in step (f) laser light is applied to said remaining tissue surrounding said cavity by said therapeutic device.

6. A surgical procedure for treating a tumor in a living body of claim 1, wherein in step (f) ionizing radiation is applied to said remaining tissue surrounding said cavity by said therapeutic device.

7. A surgical procedure for treating a tumor in a living body of claim 1, wherein in step (f) laser light and radiation are applied to said remaining tissue surrounding said cavity by said therapeutic device.

8. A surgical procedure for treating a tumor in a living body of claim 1, wherein the biodegradable positioning device is made from a porous material.

9. A surgical procedure for treating a tumor in a living body of claim 1, wherein the biodegradable positioning device is made as a scaffold or a foam obtained through sub- or supercritical gas or by heat treatment.

10. A surgical procedure for treating a tumor in a living body of claim 1, further comprising:
    inserting catheters inside the biodegradable mold; and
    placing the biodegradable mold inside the resection cavity.

11. A surgical procedure for treating a tumor in a living body of claim 1, further comprising:
    inserting catheter(s) or balloon catheter(s) inside a hollow structure formed in the biodegradable positioning device days to months after the biodegradable positioning device has been placed in the cavity.

12. A surgical procedure for treating a tumor in a living body of claim 1, further comprising:
    evaluating an appropriate therapy according to pathologic results; and delivering either an exclusive therapy or a boost therapy after external radiation using the biodegradable positioning device, several weeks or several months after the biodegradable positioning device has been placed.

13. A surgical procedure for treating a tumor in a living body of claim 1, wherein the biodegradable positioning device and at least one catheter are left inside the living body without the at least one catheter coming out through a skin of the living body, and wherein the at least one catheter is extracted through the skin only when it is decided that an additional treatment has to start.

14. A surgical procedure for treating a tumor in a living body of claim 13, wherein one end of the at least one catheter has a hole, a loop, and a screw eye that is blocked with a suture inside a structure close to a surface of the structure.

15. A surgical procedure for treating a tumor in a living body of claim 13, wherein one end of the at least one catheter has an irregular surface that is blocked with a suture once the said one end is pulled out from a structure to be treated.

16. The surgical procedure for treating a tumor in a living body of claim 1,
    wherein making the biodegradable mold of the removed portion of the tumor comprises at least one of cutting or grazing to vary the length, the width and the shape of the biodegradable positioning device.

17. A surgical procedure for treating a tumor in a living body of claim 9, wherein the biodegradable positioning device is made as a foam and the gas is $CO_2$.

* * * * *